(12) United States Patent
Arguello

(10) Patent No.: US 9,765,899 B2
(45) Date of Patent: Sep. 19, 2017

(54) DISPOSABLE DENTAL VALVE DEVICE

(71) Applicant: Stoma Ventures, LLC, St. Louis, MO (US)

(72) Inventor: Edward Arguello, Weston, FL (US)

(73) Assignee: STOMA VENTURES, LLC, St. Louis, MO (US)

(*) Notice: Subject to any disclaimer, the term of this patent is extended or adjusted under 35 U.S.C. 154(b) by 0 days.

(21) Appl. No.: 14/931,360

(22) Filed: Nov. 3, 2015

(65) Prior Publication Data

US 2017/0122443 A1    May 4, 2017

(51) Int. Cl.
   *F16K 27/06* (2006.01)
   *A61C 17/06* (2006.01)
   *F16K 5/04* (2006.01)

(52) U.S. Cl.
   CPC ............ *F16K 27/065* (2013.01); *A61C 17/04* (2013.01); *A61C 17/043* (2013.01); *F16K 5/045* (2013.01); *F16K 5/0442* (2013.01); Y10S 251/904 (2013.01)

(58) Field of Classification Search
   CPC ........ F16K 5/02; F16K 5/0207; F16K 5/0242; F16K 5/025; F16K 5/0292; F16K 5/04; F16K 5/0407; F16K 5/0442; F16K 5/045; F16K 27/06; F16K 27/062; F16K 27/065; Y10S 251/904; A61C 1/0061; A61C 17/04; A61C 17/043
   USPC ............................ 251/148, 309, 904; 433/95
   See application file for complete search history.

(56) References Cited

U.S. PATENT DOCUMENTS

| | | | | |
|---|---|---|---|---|
| 3,012,752 A | * | 12/1961 | Buck .................... | F16K 5/0414 137/625.41 |
| 3,185,179 A | * | 5/1965 | Harautuneian ..... | A61M 39/223 137/625.47 |
| 3,314,644 A | * | 4/1967 | Dwyer ................ | B29C 45/1418 251/309 |
| 3,481,367 A | * | 12/1969 | Fritz .................... | B23B 33/005 137/625.47 |
| 3,536,101 A | * | 10/1970 | Bosworth ........... | F16K 11/0853 137/315.09 |
| 3,779,513 A | * | 12/1973 | Levine ................. | F16K 5/0292 251/288 |
| 3,788,602 A | * | 1/1974 | Kitzie ................. | A61M 39/223 251/312 |
| 3,991,975 A | * | 11/1976 | Sibrava ................ | F16K 5/0478 251/309 |
| 4,015,816 A | * | 4/1977 | Semon .................. | F16K 5/0478 251/192 |
| 4,096,860 A | * | 6/1978 | McLaughlin ....... | A61M 5/1582 604/167.02 |

(Continued)

*Primary Examiner* — Mary McManmon
*Assistant Examiner* — David Colon Morales
(74) *Attorney, Agent, or Firm* — David H. Chervitz

(57) ABSTRACT

A disposable dental valve device is disclosed having a valve body having an interior, a tip receiving end having a tapered interior for receiving a tip, a hose receiving end, a lumen formed between the tip receiving end and the hose receiving end, and a partial opening formed in the valve body and a rotatable valve sealing body adapted to being inserted into the partial opening, the rotatable valve sealing body having a bore for alignment with the lumen formed between the tip receiving end and the hose receiving end, the rotatable valve sealing body having a top and a handle portion connected to the top.

20 Claims, 8 Drawing Sheets

(56) References Cited

U.S. PATENT DOCUMENTS

| | | | | |
|---|---|---|---|---|
| 4,147,184 A * | 4/1979 | Jess | F16K 5/0292 | 137/625.47 |
| 4,207,923 A * | 6/1980 | Giurtino | A61M 39/223 | 137/625.47 |
| 4,314,586 A * | 2/1982 | Folkman | A61M 39/223 | 137/625.47 |
| 4,429,856 A * | 2/1984 | Jackson | A61M 16/04 | 137/843 |
| 4,580,978 A | 4/1986 | Motola et al. | | |
| 4,705,058 A * | 11/1987 | Marklew | B29C 45/14754 | 137/15.24 |
| 4,807,666 A * | 2/1989 | Morse | F16K 5/0492 | 137/625.47 |
| 4,822,278 A * | 4/1989 | Oliva | A61C 3/00 | 294/189 |
| 4,861,266 A * | 8/1989 | Ashiku | A61C 17/043 | 433/95 |
| 4,890,817 A * | 1/1990 | Uri | F16K 27/065 | 137/327 |
| 4,966,551 A * | 10/1990 | Betush | A61C 17/043 | 433/126 |
| 5,061,180 A * | 10/1991 | Wiele | A61C 17/0208 | 433/91 |
| 5,144,972 A * | 9/1992 | Dryden | A61M 39/20 | 137/15.18 |
| 5,156,186 A * | 10/1992 | Manska | F16K 31/602 | 137/385 |
| 5,232,009 A * | 8/1993 | Jankowski | F16K 5/201 | 137/246 |
| 5,288,290 A * | 2/1994 | Brody | A61M 39/223 | 137/625.47 |
| 5,295,830 A | 3/1994 | Shen et al. | | |
| 5,480,124 A * | 1/1996 | Bartlett | A61M 1/0043 | 251/304 |
| 5,632,735 A * | 5/1997 | Wyatt | A61M 39/04 | 285/309 |
| 5,882,194 A * | 3/1999 | Davis | A61C 17/043 | 433/29 |
| 5,988,700 A * | 11/1999 | Prichard | A61M 39/10 | 138/118 |
| 6,003,553 A * | 12/1999 | Wahlberg | A61M 39/10 | 137/625.47 |
| 6,012,702 A * | 1/2000 | Heimberger | F16K 5/163 | 137/240 |
| 6,158,458 A * | 12/2000 | Ryan | A61J 1/2096 | 137/515.5 |
| 7,131,839 B2 | 11/2006 | March | | |
| 7,152,845 B2 * | 12/2006 | Carrez | F16K 35/04 | 251/208 |
| 7,559,530 B2 * | 7/2009 | Korogi | A61B 5/15003 | 251/149.6 |
| 7,695,445 B2 * | 4/2010 | Yuki | A61M 39/223 | 137/625 |
| 7,824,364 B2 * | 11/2010 | Kitani | A61M 39/045 | 604/82 |
| 9,277,978 B2 * | 3/2016 | Williams | A61C 17/04 | |
| 2003/0014842 A1 | 1/2003 | Niendorf | | |
| 2003/0098433 A1 * | 5/2003 | Henao | F16K 5/04 | 251/309 |
| 2005/0033268 A1 * | 2/2005 | Decaria | A61M 39/10 | 604/533 |
| 2006/0271015 A1 * | 11/2006 | Mantell | A61M 13/003 | 604/533 |
| 2008/0121297 A1 * | 5/2008 | Indigne | F16K 41/103 | 137/625.47 |
| 2010/0022968 A1 * | 1/2010 | Kitani | A61M 39/20 | 604/248 |
| 2011/0233437 A1 * | 9/2011 | Mattson | F16K 5/0478 | 251/309 |
| 2012/0103448 A1 * | 5/2012 | Hopf | A61M 39/223 | 137/625 |
| 2012/0259300 A1 * | 10/2012 | Bjerregaard | A61F 5/4405 | 604/327 |
| 2013/0004585 A1 | 1/2013 | Crudden et al. | | |
| 2014/0110617 A1 * | 4/2014 | Middleton | F16K 1/385 | 251/309 |
| 2014/0170595 A1 * | 6/2014 | Williams | A61C 17/04 | 433/95 |

* cited by examiner

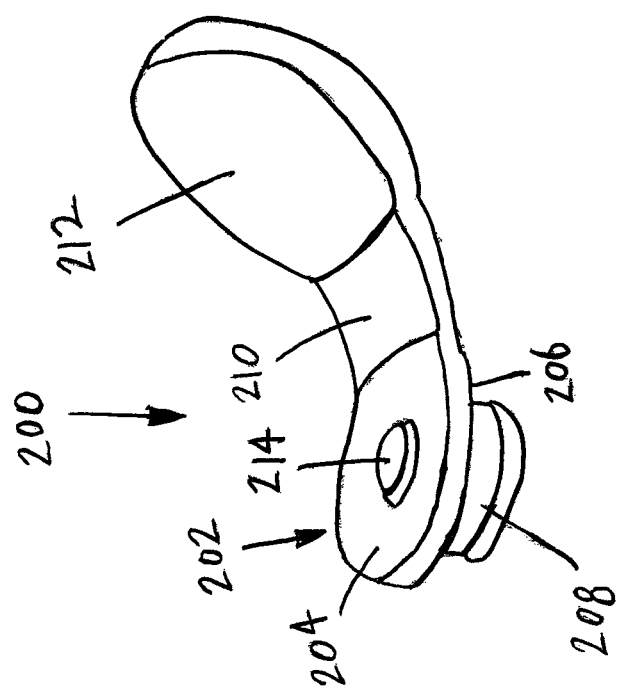

DISPOSABLE DENTAL VALVE DEVICE

BACKGROUND

This disclosure relates to a valve for a dental instrument and more particularly to a disposable dental valve device for a high volume evacuator having a tapered inlet or interior for receiving a tip.

During a dental procedure it is important to be able to remove saliva, blood, tooth fragments, metals, and other debris from the mouth of a patient. Removal of this matter allows a dentist to be able to perform a procedure in an unobstructed manner. Various systems or devices have been developed to remove liquid and solid materials from a mouth during a dental procedure. One device that is capable of removing saliva is known as a saliva ejector. A saliva ejector typically comprises a plastic flexible tube for placement in the mouth of a patient. The saliva ejector tube is connected to a valve which in turn is connected to a source of vacuum. In this manner, saliva is passed through the ejector tube and the valve to be disposed of in a sanitary manner. Once the procedure is completed, the ejector should be discarded and the valve should be sterilized by autoclaving to be used again. Although it is suggested to autoclave the valve after use, it is known that autoclaving is hardly ever done. Another device that is capable of removing solid materials is a high volume evacuator system. A high volume evacuator system generally consists of a tube that may be inserted into a mouth of a patient with the tube connected to a valve which is connected to a source of vacuum. Again, in this manner, debris may be removed from the mouth of the patient. After the dental procedure, the tube is disposed of and the valve should be sterilized for reuse. However, although it is suggested to sterilize the valve after use, it is known that this suggested procedure is hardly ever followed. As can be appreciated, the saliva ejector and the high volume evacuator are used to remove liquids and debris from a mouth of a patient to prevent a patient from swallowing or aspirating liquids and debris produced during a dental procedure.

The saliva ejector valve and the high volume evacuator valve each has a valve body having a passage and a valve sealing member. The valve sealing member has an opening that may be aligned with the passage to allow saliva and other material to pass when the valve sealing member is in an open position. When the valve sealing member is in a closed position, the source of vacuum is cut off by the valve sealing member blocking the passage through the valve body. In this manner, the saliva ejector valve and the high volume evacuator valve may be opened or closed. However, due to the construction of the valve sealing member, an opening is formed through the valve body that is perpendicular to the passage formed in the valve body. In this manner, the valve sealing member is inserted into the opening from either end of the opening when the valve is assembled.

Although these devices and systems are beneficial, one disadvantage associated with their use is that the valves may become clogged with debris during use causing the valve to malfunction. It will then be required to disassemble the valve to remove the debris. This results in a valve that cannot be used again until it is repaired and cleaned. It is also possible that debris will lodge inside the mechanism of the valve rendering the valve inoperable during a procedure. If this were to occur a new valve would have to replace the failed valve during a procedure. The valves invariably collect debris, body fluids, blood, and solids that adhere and accumulate upon the internal surfaces of the valve. The detritus that adheres to the internal surfaces of the valve can become a breeding ground for microbial contaminants. This buildup also contains microorganisms that remain in the valve system unless the valves are disassembled, the internal accumulated debris removed, and the valve sterilized.

As can be appreciated, if the valve is not cleaned and sterilized after each procedure there is the possibility of cross-contamination from one patient to another patient. In order to control infection and disease, the valve must be removed from service, disassembled, cleaned, sterilized, reassembled, checked, and then returned to service. To complicate matters, the valve may have various O-rings that need to be replaced in order for the valve to function properly. For example, the valve sealing member may include two O-rings that assist in holding the valve sealing member within the opening formed in the valve body. When disassembling the valve sealing member from the valve body, it is possible that the O-rings may become damaged. If this were to occur then the O-rings would have to be replaced. It is also possible that the O-rings may deteriorate over time and air may leak through the opening and the valve sealing member. If this were to occur then it is possible that the valve and the valve sealing member may malfunction during a dental procedure or operation. For example, the valve sealing member may be ejected from the valve body and any saliva, liquid, blood, or debris may spray out of the opening where the valve sealing member should be. Malfunctioning of the valve during an operation should be avoided because the operation will have to be paused or stopped and the operating room will have to be cleaned.

Another disadvantage of the use of a valve is that once a procedure is completed and the valve is removed, there is considerable noise generated by the source of vacuum. Although the source of vacuum may be turned off, the shutoff valve for the source of vacuum may be at a remote location. This results in having to leave the operating area to shut down the source of vacuum. Further, when the source of vacuum is required again, the shutoff valve will require being turned on again. For a system that does not have multiple shutoff valves this could impact other procedures that are pending. Also, if there is a local shutoff valve, this valve may not be in easy reach which would require moving from the patient.

As pointed out above, a further disadvantage associated with the use of these known valves is that there is the possibility of cross-contamination between patients and/or dental care professionals. In order to prevent cross-contamination it becomes necessary to process these valves by cleaning and decontamination. Cleaning requires that all of the debris be removed from the valve as well as any organic and inorganic contamination. Removal of debris and contamination may be achieved either by scrubbing with a surfactant, detergent, and water, or by an automated process using chemical agents. One example of an automated process is the use of an ultrasonic cleaner. The valve also needs to be sterilized after debris and contaminants are removed. Since the valves are constructed of metal they are heat-tolerant and may be sterilized by use of such methods such as steam under pressure (autoclaving), dry heat, or unsaturated chemical vapor. As can be appreciated, protecting against cross-contamination can be an expensive and time consuming proposition. Further, as noted above, the valves contain a number of O-rings that may need to be replaced. In order to accomplish this, an inventory of O-rings needs to be maintained. Also, in order to replace some of the O-rings, a lubricant may have to be used. Again, the lubricant will have to be inventoried so that a supply is readily available for use by service technicians. Having to inventory various supplies that may be required to service such valves is a cumbersome operation that many healthcare facilities may want to avoid.

Another problem associated with the use of high volume evacuator is that there are a number of manufacturers that produce the tip that is inserted into a mouth of a patient. The tips vary in size, shape, and stiffness and there is no standardization of the tip between manufacturers. Also, there is the possibility that a manufacturer may produce tips that do not conform to the manufacturer's specifications. In this case, there may be differences in the same tip manufactured by the same manufacturer. Due to this, a dental valve device requires the use of an O-ring or other elastic member in order to hold or secure a tip in place and to establish a seal between the valve device and the tip. The O-ring is used to hold or secure the tip in place during an operation or dental procedure. As has been previously indicated, over time the O-ring will deteriorate due to use and cleaning and will have to be replaced. The O-ring that holds the tip in place may be a different size than the O-rings that hold the valve sealing member in place. This means that an inventory of different sized O-rings must be available to a technician servicing the dental valve device. There is also the possibility that the O-ring may fail during a dental procedure and the tip will become dislodged from the dental valve device.

Therefore, it would be desirable to have a valve for a dental instrument that is capable of securing a tip in place so that the vacuum seal between the valve and the tip does not malfunction during a dental operation. It would also be advantageous to have a valve for a dental instrument that is easy to install or insert a tip of any size, shape, or hardness therein. It would further be desirable to have a valve that is disposable and can accept a tip of any size, shape, or hardness.

BRIEF SUMMARY

In one form of the present disclosure, a disposable dental valve device comprises a valve body having an interior, a tip receiving end having a tapered interior for receiving a tip, a hose receiving end, a lumen formed between the tip receiving end and the hose receiving end, and a partial opening formed in the valve body and a rotatable valve sealing body adapted to being inserted into the partial opening, the rotatable valve sealing body having a bore for alignment with the lumen formed between the tip receiving end and the hose receiving end, the rotatable valve sealing body having a top and a handle portion connected to the top.

In another form of the present disclosure, a disposable dental valve device comprises a valve body having an interior, a tip receiving end having a tapered interior for receiving a tip, a hose receiving end, a lumen formed between the tip receiving end and the hose receiving end, a partial opening formed in the valve body with the partial opening having an annular channel formed in the interior and a bottom receiving end, and a rotatable valve sealing body adapted to being inserted into the partial opening and contacting the bottom receiving end, the rotatable valve body having a bore having a first concave opening and a second concave opening with the bore and the openings for alignment with the lumen formed between the tip receiving end and the hose receiving end, the first and second concave openings forming a lower annular ring for engagement with the bottom receiving end and the interior of the valve body, the rotatable valve body having a top having an annular ridge portion with the annular ridge portion for insertion into the annular channel formed in the interior of the valve body to secure the rotatable valve sealing body within the valve body and a handle portion connected to the top with movement of the handle capable of positioning the bore in alignment with the lumen.

In yet another form of the present disclosure, a disposable dental valve device kit comprises a valve body having an interior, a tip receiving end having a tapered interior for receiving a tip, a hose receiving end, a lumen formed between the tip receiving end and the hose receiving end, and a partial opening formed in the valve body, a rotatable valve sealing body adapted to being inserted into the partial opening, the rotatable valve sealing body having a bore for alignment with the lumen formed between the tip receiving end and the hose receiving end, the rotatable valve sealing body having a top and a handle portion connected to the top, and a cap device for insertion into a hose connected to a source of vacuum.

The present disclosure provides a disposable dental valve device for a dental instrument that is suitable for one time use and may be discarded after use.

The present disclosure provides a disposable dental valve device that is easy to install on a hose connected to a source of vacuum and have a tip installed in a tapered tip receiving end of the device for securing the tip therein.

The present disclosure provides a valve for a dental instrument that is small, lightweight, easy to handle, easy to install, and easy to operate.

The present disclosure also provides a valve for a dental instrument which is of simple construction and design and which can be easily employed with highly reliable results.

The present disclosure is related to a disposable dental valve device that does not require sterilization and prevents against cross-contamination.

The present disclosure provides a disposable dental valve device that may have an antimicrobial agent or chemical incorporated into the device to prevent any bacterial growth on the device. The antimicrobial agent or chemical may also be a coating applied to the disposable dental valve device.

The present disclosure is related to a disposable dental valve device that may be constructed of plastic that is recyclable or biodegradable to reduce the cost of the device and to allow the device to be disposable and discarded after a single use.

The present disclosure provides a disposable dental valve device that further includes a cap device that may be used to cap off a source of vacuum when the device is removed from a hose connected to the source of vacuum to reduce or eliminate any sound or noise associated with the source of vacuum.

The present disclosure is related to a disposable dental valve device that has a valve sealing body that is easy to manipulate during a dental operation to open or close the valve.

The present disclosure is also directed to a disposable dental valve device that has a tip receiving end having a tapered interior that is capable of accepting tips of varying sizes, shapes, and hardness.

The present disclosure is further directed to a disposable dental valve device that is constructed using a minimal number of parts to reduce the cost of manufacturing the disposable dental valve device.

These and other advantages of the present disclosure will become apparent after considering the following detailed specification in conjunction with the accompanying drawings, wherein:

BRIEF DESCRIPTION OF THE DRAWINGS

FIG. 8 is a perspective view of cap device constructed according to the present disclosure.

DETAILED DESCRIPTION OF PREFERRED EMBODIMENTS

Figure 1:
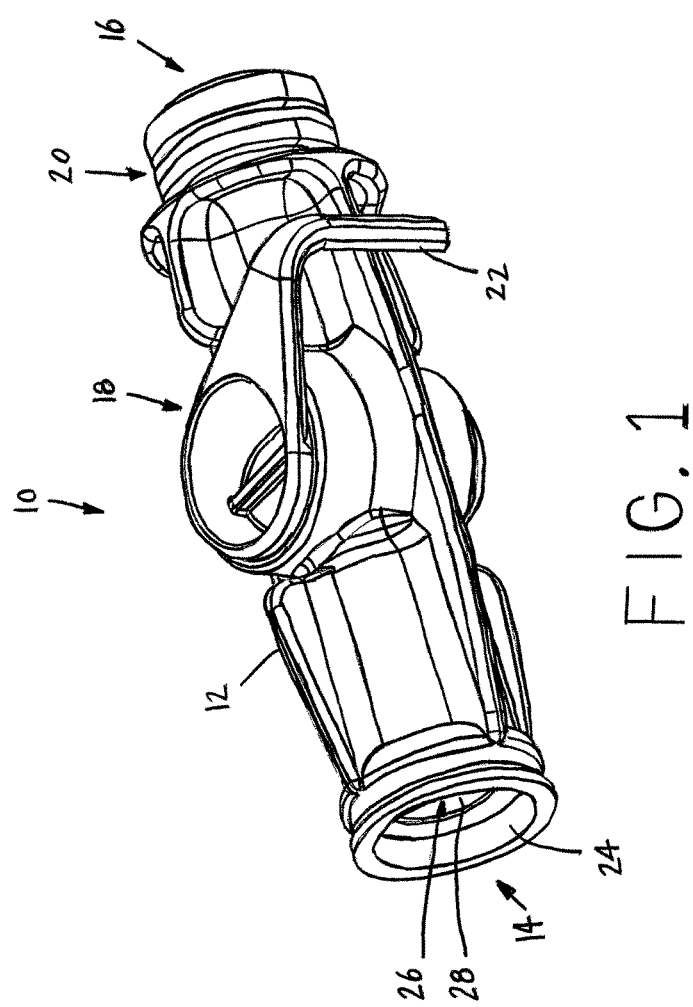
FIG. 1 is a perspective view of a disposable dental valve device constructed according to the present disclosure.

Referring now to the drawings, wherein like numbers refer to like items, number 10 identifies a disposable dental valve device for use with a dental system constructed according to the present disclosure. With reference now to FIG. 1, the valve 10 comprises a valve body 12 having a tip receiving end 14, a hose receiving end 16, and a rotatable valve sealing body 18. The tip receiving end 14 is adapted to receive an evacuator tip device (not shown) such as a high volume evacuator. The hose receiving end 16 is adapted to receive a vacuum line or a hose (not shown) which is connected to a suction system (also not shown). The hose receiving end 16 also has a circumferential channel 20 that is adapted to accept an O-ring (not shown). The O-ring is used to further secure a hose or a tailpiece to the hose receiving end 16. It is also possible that the hose receiving end 16 may incorporate a structure to secure a hose to the end 16 without the use of the channel 20 or the requirement for an O-ring. For example, the end 16 may be barbed so that the barbs may hold a hose thereon. The device 10 is constructed of material that allows the device 10 to be disposable and suitable for one time use. The device 10 also has a handle 22 for manual operation of the rotatable valve sealing body 18 of the device 10. Manual operation of the handle 22 will open the device 10, close the device 10, or partially open the device 10, as will be discussed more fully herein. As can be appreciated, a suction system provides suction through an evacuator tip device, the device 10, and a hose so that any debris or saliva that is introduced into an evacuator tip device is removed through an evacuator tip device, the valve 10, and a hose when the rotatable valve sealing body 18 of the device 10 is in an open state or a partially open state. The valve body 12 also has an opening 24 at the tip receiving end 14 and a passage or lumen 26 formed in the valve body 12. The lumen 26 continues through the valve body 12 to the hose receiving end 16. As will be discussed more fully herein, the tip receiving end 14 has an interior surface 28 that is tapered so that the device 10 is capably of receiving various sized and shaped evacuator tip devices. In this manner, there is no need for an O-ring to be used or for the device 10 to have engineered therein an interior annular ring for receiving the O-ring for retaining a tip therein.

Figure 2:
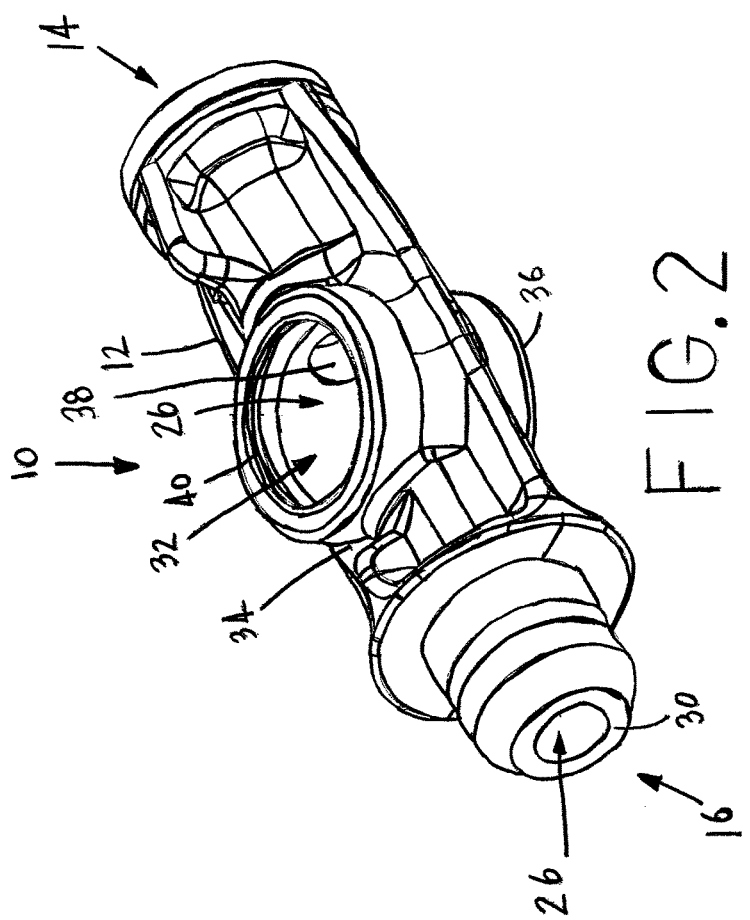
FIG. 2 is a perspective view of a disposable dental valve device constructed according to the present disclosure with a valve sealing body removed.

With reference now to FIG. 2, the device 10 is shown with the rotatable valve sealing device 18 being removed. The valve body 12 has the lumen 26 and an opening 30 at the hose receiving end 16. As has been described, the lumen 26 continues through the valve body 12 to the tip receiving end 14. The valve body 12 also has a partial opening 32 formed on a top side 34 of the valve body 12. The partial opening 32 does not go all the way through the valve body 12. The partial opening 32 is blocked by a bottom 36 of the valve body 12. An opening 38 is also shown in the lumen 26 between the tip receiving end 14 and the opening 32. An annular channel or ring 40 is formed in the opening 32 which is used to retain the rotatable valve sealing device 18 in place, as will be explained in further detail herein.

Figure 3:
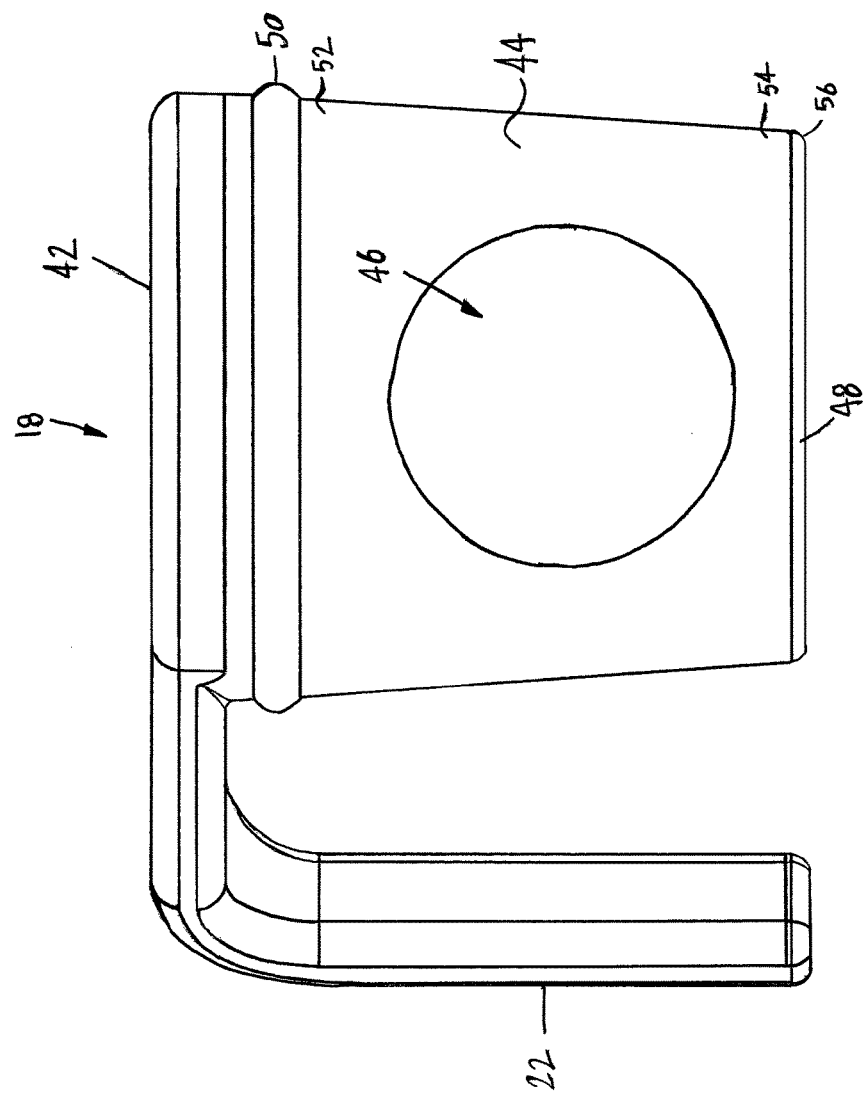
FIG. 3 a side perspective view of a valve sealing body constructed according to the present disclosure.

FIG. 3 shows the rotatable valve sealing body 18 removed from the device 10 in an open position. The rotatable valve sealing body 18 has a top 42, a central body portion 44 having a bore 46, and a bottom 48. The handle 22 is part of the top 42. The central body portion 44 also has an annular ridge portion 50 near the top 42. The ridge portion 50 is capable of fitting into the ring 40 (FIG. 2) in a snap fit engagement to secure the rotatable valve sealing body 18 within the valve body 12. The central body portion 44 has an upper end 52 and a lower end 54 with the central body portion 44 tapering inwardly from the upper end 52 toward the lower end 54. The tapering of the central body portion 44 facilitates the insertion and removal of the rotatable valve sealing body 18 from the device 10. The bottom 48 has a chamfer 56 which also assists in insertion of the rotatable valve sealing body 18. The bore 46 is adapted to be aligned with the lumen 26 of the valve body 12. When the bore 46 is aligned with the lumen 26, the device 10 is in an open position and the source of vacuum will draw any fluid or debris from the tip receiving end 14 through the lumen 26 and the bore 46 and out through the hose receiving end 16. In this manner, fluid and debris may be removed from a mouth during a dental procedure or operation. Although the ridge 50 is shown, it is possible that an annular ring may be formed in the central body portion 44 and an O-ring may be used to hold the valve sealing body 18 in place. Also, although one ridge 50 is depicted, it is contemplated that another ridge 50 may be formed on the central body portion 44 near the bottom 48 and another ring 40 be formed in the opening 30 near the bottom 36 to receive the second ridge 50 to further secure the valve sealing body 18 in place.

Figure 4:
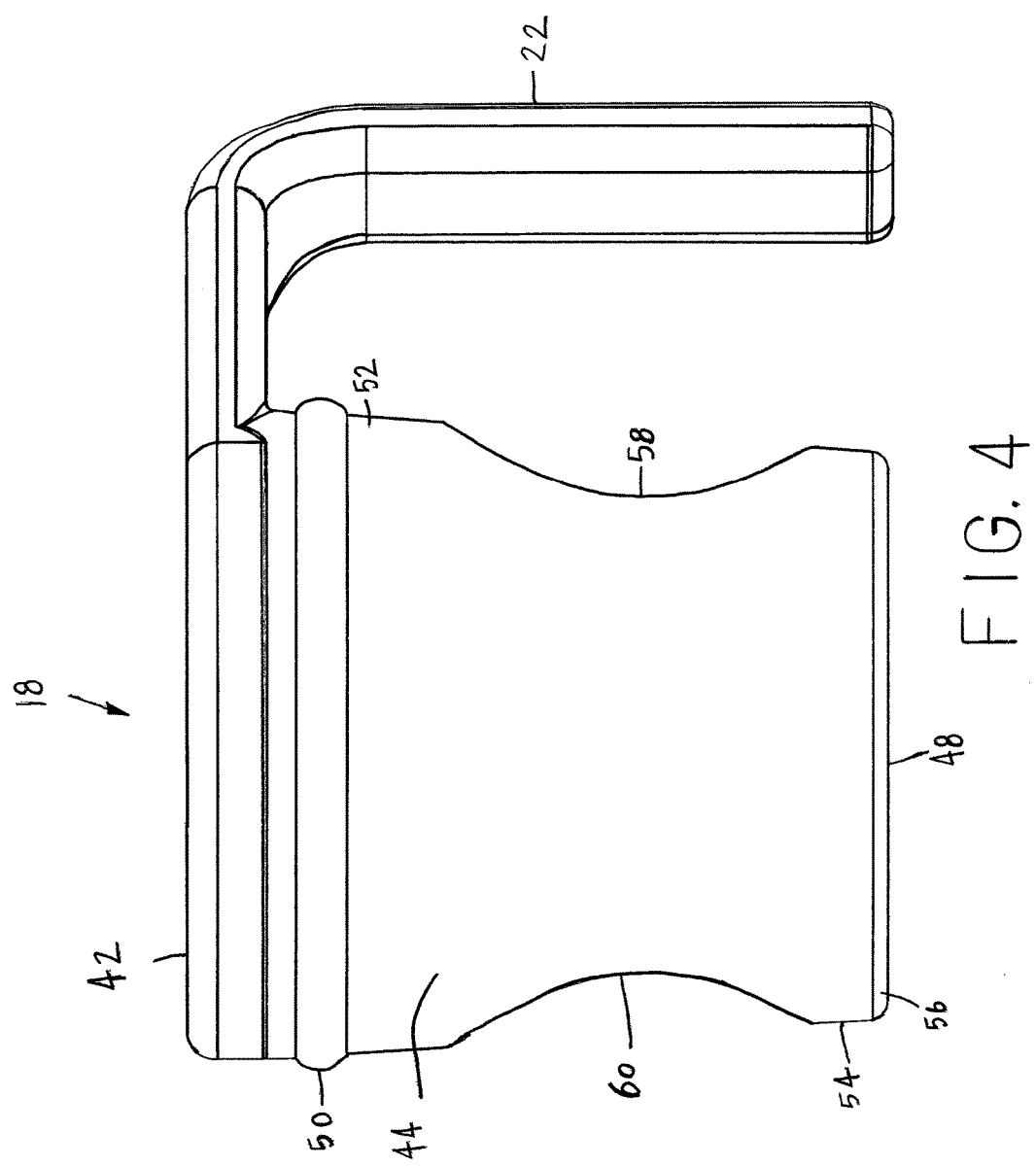
FIG. 4 is another side view of the valve sealing body constructed according to the present disclosure.

Referring now to FIG. 4, the rotatable valve sealing body 18 is illustrated removed from the device 10 in a closed position. The rotatable valve sealing body 18 has the top 42, the central body portion 44 having a first opening 58 and a second opening 60, and the bottom 48 having the chamfer 56. The openings 58 and 60 are aligned with the bore 46 (FIG. 3). When the rotatable valve sealing body 18 is in the closed position, the central body portion 44 will block any air flow through the valve body 12. In essence, the bore 46 is no longer aligned with the lumen 26 formed in the valve body 12. The rotatable valve sealing body 18 is moved into the closed position by use of the handle 22. The openings 58 and 60 are concave which allows the rotatable valve sealing body 18 to rotate. The central body portion 44 is also shown having the upper end 52 and the lower end 54. The central body portion 44 tapers inwardly from the upper end 52 toward the lower end 54. The upper end 52 has a width and the lower end 54 has a width with the width of the upper end 52 being greater than the width of the lower end 54.

Figure 5:
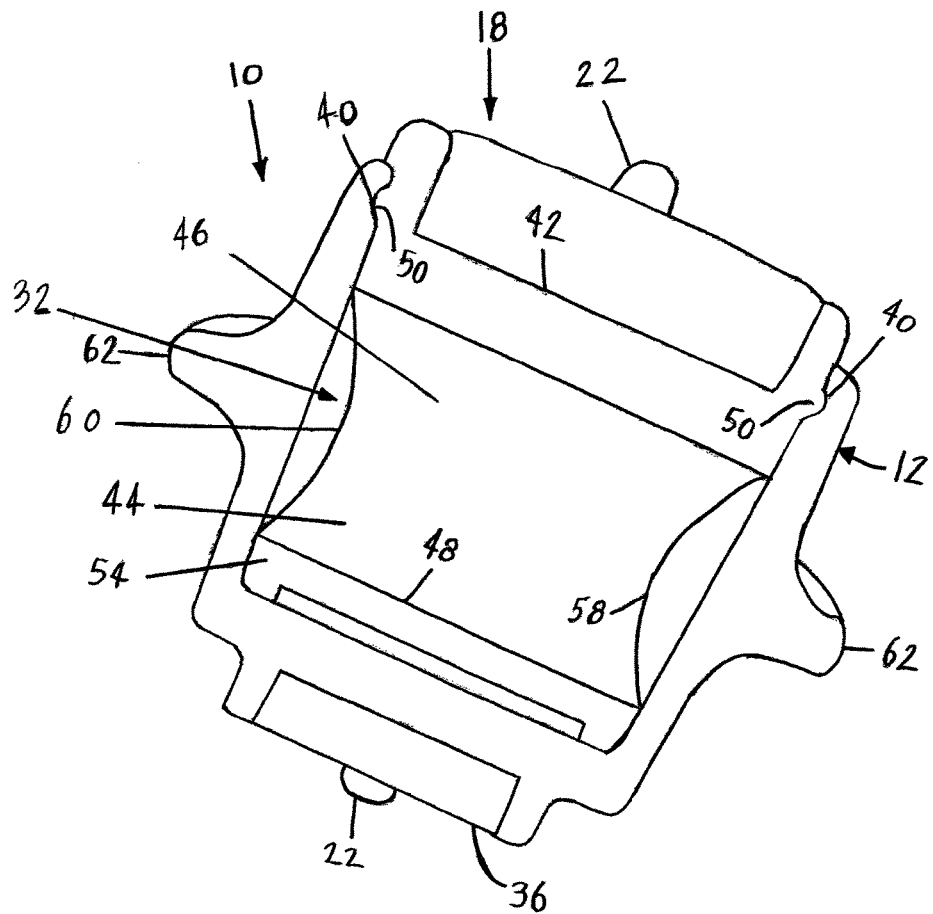
FIG. 5 is a cross-sectional view of the disposable dental valve device constructed according to the present disclosure.

FIG. 5 is a cross-sectional view of the disposable dental valve device 10 with the rotatable valve sealing body 18 in the closed position. The device 10 has the valve body 12 having the rotatable valve sealing body 18 mounted therein. The rotatable valve sealing body 18 is held in place by use of the ridge 50 being snapped into place within the ring 40. The bottom 48 of the rotatable valve sealing body 18 is adjacent to the bottom 36 of the valve body 12. In this manner, the rotatable valve sealing body 18 is able to rotate within the valve body 12. Further, the bottom 36 ensures that the opening 32 (FIG. 2) is a partial opening and the opening 32 does not go all the way through the valve body 12. The opening 32 reduces the risk that the rotatable valve sealing body 18 will become disengaged during use or that the valve 10 will fail during use. The rotatable valve sealing body 18 also has the bore 46 formed therein between the openings 58 and 60. As previously described, the openings 58 and 60 are concave and the sealing body 18 has the lower end 54 of the central body portion 44 that is frictionally engaged near the bottom 36 within the opening 32 formed in the valve body 12. The valve body 12 also has exterior ribs 62 that add strength to the valve body 12 and also assist in forming the valve body 12. The handle 22 is also shown as being part of the device 10.

Figure 6:
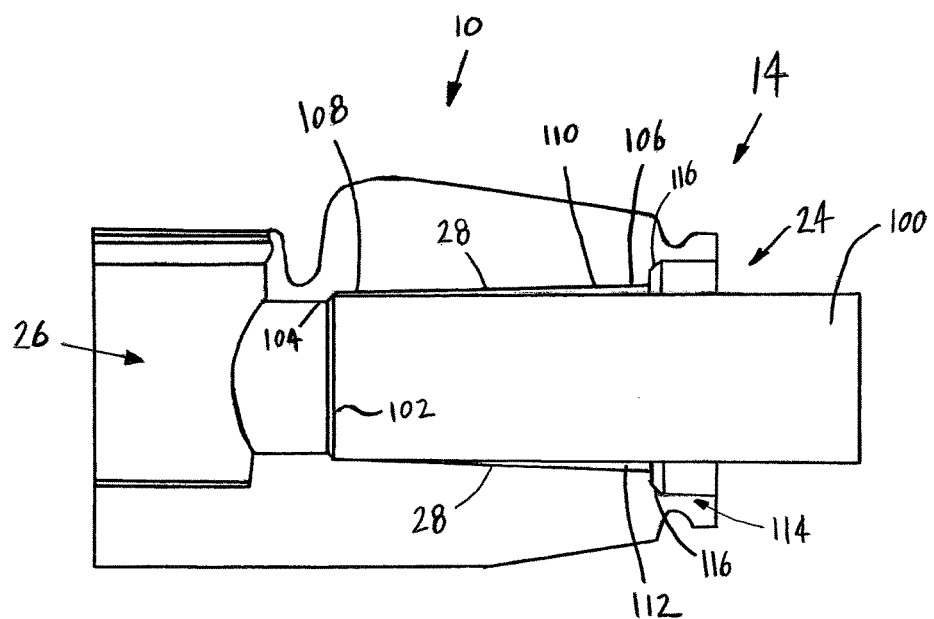
FIG. 6 is an enlarged partial cross-sectional view of a disposable dental valve device constructed according to the present disclosure having a tip inserted therein.

With reference now to FIG. 6, an enlarged partial cross-sectional view of the tip receiving end 14 of the device 10 is shown having an evacuator tip 100 inserted therein. The evacuator tip 100 is narrow enough to be inserted so that a back end 102 of the tip 100 is adjacent to a back wall portion 104 of the tip receiving end 14. The back wall portion 104 serves as a stop or limit as to how far the tip 100 may be inserted into the device 10. The interior surface 28 is tapered inwardly from a front end 106 toward a back end 108. An upper gap 110 is present between the tip 100 and the interior surface 28 and a lower gap 112 is also present between the tip 100 and the interior surface 28. In this manner, a press fit or frictional engagement is created between the interior surface 28 and the tip 100. This secures or holds the tip 100 in place within the tip receiving end 14 during a dental procedure or operation. Further, the front end 106 is wider or has a greater diameter than the back end 108 and this provides for the inward taper of the interior surface 28. The opening 24 has a length 114 with the length 114 of the opening 24 extending into the lumen 26 to a chamfered section 116.

Figure 7:
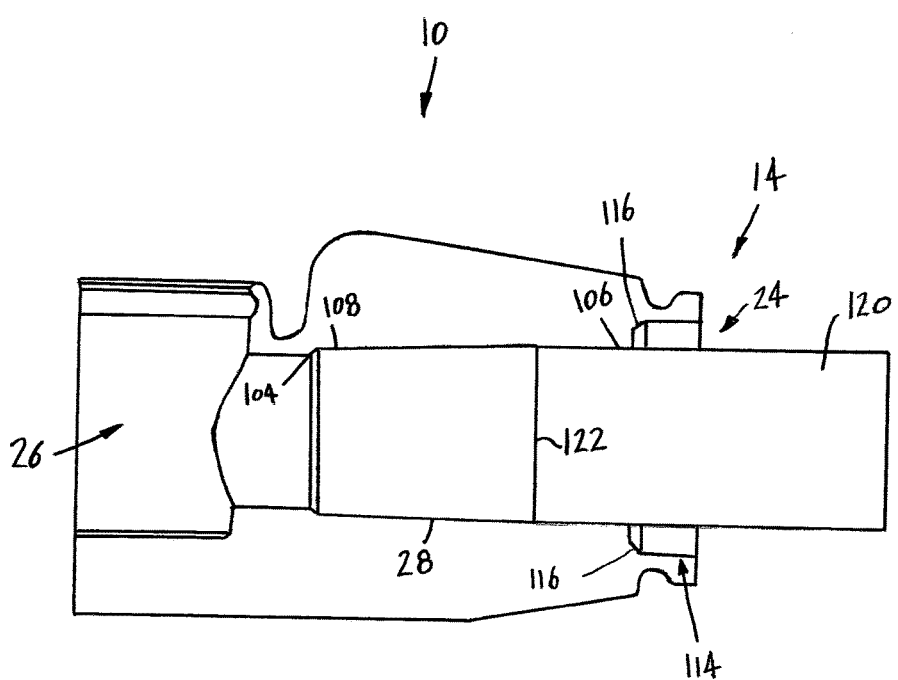
FIG. 7 is an enlarged partial cross-sectional view of a disposable dental valve device constructed according to the present disclosure having a different tip inserted therein.

FIG. 7 shows an enlarged partial cross-sectional view of the tip receiving end 14 of the device 10 having another evacuator tip 120 inserted therein. The tip 120 is different than the tip 100 in that the tip 120 is thicker or has a larger diameter. As can be appreciated, due to the larger diameter, the tip 120 is not able to contact the back wall portion 104 due to the taper of the interior surface 28 capturing the tip 120 and a back end 122 of the tip 120. The interior surface 28 is also shown having the front end 106 being tapered toward a back end 108. The tapering of the interior surface 28 allows for different sized, shaped, and hardness tips 100 and 120 to be inserted into the tip receiving end 14 and to be held in place. Since manufacturers may produce tips having various sizes, shapes, and hardness, the device 10 will be capable of receiving such different tips and there is no need for an O-ring or other elastic member for holding and securing a tip in place. The opening 24 has the length 114 with the length 114 of the opening 24 extending into the lumen 26 to the chamfered section 116.

Referring to FIG. 8, a cap device 200 is depicted which is used to be placed over the opening of a hose when the device 10 is removed from the hose to remove or dispose the device 10. In this manner, the opening of the hose will be physically blocked to shut off any air from rushing into the hose to silence any noise produced by the suction system or a source of vacuum. The cap device 200 is sized and shaped to fit over the opening of the hose. The cap device 200 may be constructed of any suitable material such as rubber or plastic. The valve device 10 may include the cap device 200 so that when valve device 10 is being removed from the hose for disposal after use the cap device 200 may be placed over the opening of the hose. The cap device 200 comprises a body portion 202 having a top side 204 and a bottom side 206 with the bottom side 206 having a plug portion 208. A central portion 210 is connected between the body portion 202 and a pull 212. The top side 204 has a raised portion or bump 214. The plug portion 208 is inserted into the opening of the hose or flexible tubing connected to a suction source. The pull 212 is used to be grasped by a hand to remove the plug portion 208 and the cap device 200 from the hose when a new disposable dental valve device 10, 60, or 100 is to be used. The plug portion 208 may be of a sufficient size and shape to plug an opening associated with a hose attached to a source of suction. The cap device 200 may also be provided separately from the device 10. As has been indicted above, it is also possible that the cap device 200 may be provided as a kit with the device 10.

In operation of the device 10, the hose receiving end 16 of the device 10 is placed on to a hose connected to a suction system and an evacuator tip is inserted into the tip receiving end 14 and then placed in a mouth of a dental patient. The handle 22, which may include an indicator to indicate the closed position and the open position, is manually operated to open the device 10. Once in the open position, air is allowed to flow through the tip, the tip receiving end 14, the lumen 26, the bore 46 of the rotatable valve sealing body 18, the hose receiving end 16 and into a suction system. When suction is not needed during a dental procedure, the handle 22 is moved to the closed position. Further, once a dental procedure has been completed, the handle 22 is moved to the closed position, the device is easily separated from the hose, and the cap device 200 is placed over the opening associated with the hose. The cap device 200 will block any air from being sucked into the hose and this silences any noise that is generated by the source of vacuum or the suction system. Once the device 10 is disconnected from the hose, the device 10 may be disposed of by any suitable manner. A new device 10 is then connected to the hose after the cap device 200 is removed. With the new valve 10 installed, another dental procedure may be initiated.

The disposable dental valve device 10 may be formed of any suitable material such as plastic, polyethylene, and high density polyethylene or any other suitable material that is disposable and recyclable. Any suitable plastic may be used to construct the device 10 so that the device 10 may withstand use in a dental operation or procedure. It is also possible and contemplated to incorporate an antimicrobial agent or chemical in the plastic or to provide a coating of an antimicrobial agent on the plastic to further prevent cross-contamination when using the device 10.

From all that has been said, it will be clear that there has thus been shown and described herein a disposable dental valve device which fulfills the various advantages sought therefore. It will become apparent to those skilled in the art, however, that many changes, modifications, variations, and other uses and applications of the subject disposable dental valve device are possible and contemplated. All changes, modifications, variations, and other uses and applications which do not depart from the spirit and scope of the disclosure are deemed to be covered by the disclosure, which is limited only by the claims which follow.

What is claimed is:

1. A disposable dental valve device comprising:
a valve body having an interior, a tip receiving end having an opening, a hose receiving end, a lumen formed between the tip receiving end and the hose receiving end, and a partial opening formed in the valve body, the tip receiving end opening having a first length with the first length of the tip receiving end opening extending into the lumen to a chamfered section, the chamfered section having a second length with the first length being greater than the second length, the tip receiving end opening have a first diameter, a front end adjacent to the chamfered section, a back wall portion, an interior surface formed between the front end and the back wall portion with the interior surface being tapered inwardly from the front end toward the back wall portion, the front end having a front end diameter, the back wall portion having a back wall portion diameter with the front end diameter being greater than the back wall portion diameter and the first diameter being greater than the front end diameter; and
a rotatable valve sealing body adapted to being inserted into the partial opening formed in the valve body, the rotatable valve sealing body having a bore for alignment with the lumen formed between the tip receiving end and the hose receiving end, the rotatable valve sealing body having a top and a handle portion connected to the top.

2. The disposable dental valve device of claim 1 wherein the interior surface has a third length between the front end and the back wall portion with the third length being greater than the second length.

3. The disposable dental valve device of claim 2 wherein the third length is greater than the first length.

4. The disposable dental valve device of claim 1 wherein the first diameter is greater than the back wall portion diameter.

5. The disposable dental valve device of claim 1 wherein the back wall portion stops a tip inserted therein from entering into the partial opening formed in the valve body.

6. The disposable dental valve device of claim 1 wherein the chamfered section directs a tip inserted therein into the interior surface formed between the front end and the back wall portion.

7. The disposable dental valve device of claim 1 wherein the disposable dental valve device is constructed of plastic.

8. The disposable dental valve device of claim 1 wherein an antimicrobial agent is incorporated into the disposable dental valve device.

9. A disposable dental valve device comprising:
a valve body having an interior, a tip receiving end having an opening, a hose receiving end, a lumen formed between the tip receiving end and the hose receiving end, a partial opening formed in the valve body with the partial opening having an annular channel formed in the interior and a bottom receiving end, the tip receiving end opening having a first length with the first length of the tip receiving end opening extending into the lumen to a chamfered section, the chamfered section having a second length with the first length being greater than the second length, the tip receiving end opening have a first diameter, a front end adjacent to the chamfered section, a back wall portion, an interior surface formed between the front end and the back wall portion with the interior surface being tapered inwardly from the front end toward the back wall portion, the front end having a front end diameter, the back wall portion having a back wall portion diameter with the front end diameter being greater than the back wall portion diameter and the first diameter being greater than the front end diameter; and
a rotatable valve sealing body adapted to being inserted into the partial opening formed in the valve body and contacting the bottom receiving end, the rotatable valve body having a bore having a first concave opening and a second concave opening with the bore and the openings for alignment with the lumen formed between the tip receiving end and the hose receiving end, the first and second concave openings forming a lower annular ring for engagement with the bottom receiving end and the interior of the valve body, the rotatable valve body having a top having an annular ridge portion with the annular ridge portion for insertion into the annular channel formed in the interior of the valve body to secure the rotatable valve sealing body within the valve body and a handle portion connected to the top with movement of the handle capable of positioning the bore in alignment with the lumen.

10. The disposable dental valve device of claim 9 wherein the interior surface has a third length between the front end and the back wall portion with the third length being greater than the second length.

11. The disposable dental valve device of claim 10 wherein the third length is greater than the first length.

12. The disposable dental valve device of claim 9 wherein the first diameter is greater than the back wall portion diameter.

13. The disposable dental valve device of claim 9 wherein the back wall portion stops a tip inserted therein from entering into the partial opening formed in the valve body.

14. The disposable dental valve device of claim 9 wherein the chamfered section directs a tip inserted therein into the interior surface formed between the front end and the back wall portion.

15. A disposable dental valve device kit comprising:
a valve body having an interior, a tip receiving end having an opening, a hose receiving end, a lumen formed between the tip receiving end and the hose receiving end, and a partial opening formed in the valve body, the tip receiving end opening having a first length with the first length of the tip receiving end opening extending into the lumen to a chamfered section, the chamfered section having a second length with the first length being greater than the second length, the tip receiving end opening have a first diameter, a front end adjacent to the chamfered section, a back wall portion, an interior surface formed between the front end and the back wall portion with the interior surface being tapered inwardly from the front end toward the back wall portion, the front end having a front end diameter, the back wall portion having a back wall portion diameter with the front end diameter being greater than the back wall portion diameter and the first diameter being greater than the front end diameter;
a rotatable valve sealing body adapted to being inserted into the partial opening formed in the valve body, the rotatable valve sealing body having a bore for alignment with the lumen formed between the tip receiving end and the hose receiving end, the rotatable valve sealing body having a top and a handle portion connected to the top; and
a cap device for insertion into a hose connected to a source of vacuum.

16. The disposable dental valve device kit of claim 15 wherein the cap device comprises a body portion having a top side and a bottom side with the bottom side having a plug portion, a pull, and a central portion connected between the body portion and the pull.

17. The disposable dental valve device of claim 15 wherein the interior surface has a third length between the front end and the back wall portion with the third length being greater than the second length.

18. The disposable dental valve device of claim 17 wherein third length is greater than the first length.

19. The disposable dental valve device of claim 17 wherein the back wall portion stops a tip inserted therein from entering into the partial opening formed in the valve body.

20. The disposable dental valve device of claim 15 wherein the chamfered section directs a tip inserted therein into the interior surface formed between the front end and the back wall portion.

\* \* \* \* \*